United States Patent
Scharfenberg

(10) Patent No.: US 7,588,113 B2
(45) Date of Patent: Sep. 15, 2009

(54) WHEEL DRIVE

(75) Inventor: Stephan Scharfenberg, Tüttleben (DE)

(73) Assignee: ZF Friedrichshafen AG, Friedrichshafen (DE)

( * ) Notice: Subject to any disclaimer, the term of this patent is extended or adjusted under 35 U.S.C. 154(b) by 407 days.

(21) Appl. No.: 10/587,788

(22) PCT Filed: Jan. 19, 2005

(86) PCT No.: PCT/EP2005/000486

§ 371 (c)(1),
(2), (4) Date: Jul. 31, 2006

(87) PCT Pub. No.: WO2005/077696

PCT Pub. Date: Aug. 25, 2005

(65) Prior Publication Data
US 2007/0123381 A1   May 31, 2007

(30) Foreign Application Priority Data
Feb. 11, 2004  (DE) ................ 10 2004 006 722
May 12, 2004  (DE) ................ 10 2004 023 341

(51) Int. Cl.
*B60K 17/30* (2006.01)
(52) U.S. Cl. .................... 180/253; 475/156
(58) Field of Classification Search ............. 180/252, 180/253, 254, 234, 245, 371, 372; 475/153, 475/156
See application file for complete search history.

(56) References Cited

U.S. PATENT DOCUMENTS

| 2,779,425 | A | * | 1/1957 | Miller .................... 180/21 |
| 4,234,809 | A | * | 11/1980 | Burenkov et al. ........... 310/105 |
| 4,513,839 | A | * | 4/1985 | Nieminski et al. .......... 180/253 |
| 4,616,730 | A | | 10/1986 | Strehler et al. |
| 5,121,018 | A | * | 6/1992 | Oldakowski ............. 310/77 |
| 5,128,598 | A | * | 7/1992 | Avitan .................. 318/587 |
| 6,032,468 | A | | 3/2000 | Fetescu et al. |
| 6,367,571 | B1 | | 4/2002 | Schwarz |

FOREIGN PATENT DOCUMENTS

| DE | 34 20 146 A1 | 12/1985 |
| DE | 41 10 792 A1 | 10/1992 |
| DE | 691 09 453 T | 9/1995 |
| DE | 197 20 789 A1 | 11/1998 |
| DE | 199 04 552 A1 | 9/1999 |
| DE | 199 49 351 A1 | 7/2001 |
| DE | 101 30 100 A1 | 1/2003 |
| EP | 0 507 137 A1 | 10/1992 |
| GB | 2055338 A * | 3/1981 |

* cited by examiner

*Primary Examiner*—Roger L Pang
*Assistant Examiner*—Derek D Knight
(74) *Attorney, Agent, or Firm*—Davis & Bujold, P.L.L.C.

(57) ABSTRACT

A wheel drive has one first prime mover (1), one brake (19) and one second prime mover (8) which are co-axially disposed. Via a reduction gear (4), the first prime mover (1) drives a drive wheel (7) for the traction gear, the second prime mover (8), via a planetary transmission (11), drive the prime mover in direction of a steering motion.

9 Claims, 5 Drawing Sheets

WHEEL DRIVE

This application is a national stage completion of PCT/EP2005/000486 filed Jan. 19, 2005 which claims priority from German Application Serial No. 10 2004 006 722.8 filed Feb. 11, 2004.

FIELD OF THE INVENTION

According to the kind defined in detail in the preamble of claim 1, the invention relates to a wheel drive.

BACKGROUND OF THE INVENTION

Wheel drives, particularly one-wheel power packs for industrial lift trucks, generically have one prime mover which, via a reduction gear, drives the drive wheel and a steering motor by way of a drive wheel that can turn a steering axle around to perform a steering motion. The installation space for the wheel drive and the steering mechanism is extremely limited here.

DE 34 20 146 A1 discloses a wheel drive for an industrial lift truck where one drive wheel is actuated via a reduction gear by a prime mover and a steering motor, via a chain, can turn the drive wheel around a steering axis of rotation so as to perform a steering motion. The steering motor is separately placed here next to the traction motor whereby a large installation space is needed.

The problem on which this invention is based is to provide a wheel drive, in particular for a n industrial lift truck, in which the traction motor actuates the vehicle wheel and the wheel drive is rotatably actuatable via a steering motor around a steering axis of rotation and which is compactly and economically constructed.

SUMMARY OF THE INVENTION

According to the invention, the traction motor, the steering motor and the brake, which brakes the wheel drive, are co-axially disposed. The brake is preferably between the traction motor and the steering motor. By using a steering gear, which preferably is likewise situated co-axially relative to the steering motor, it is possible to use a compact steering motor.

In another development of the invention, the traction motor, the brake and the steering motor are located in a common housing whereby a further reduction of installation space needed is possible and an economical solution is obtained.

In one other development of the invention, the brake is designed as so-called negative brake whereby the brake is actuatable by spring tension in closing direction and by hydraulic pressure or electric actuation of a magnetic coil, it can be actuated in opening direction. The brake can be designed as friction disc brake, it being possible to place the friction linings either in one space filled with lubricant, or also to design it as dry-operating disc brake without lubricant.

In another development, the drive shaft of the traction motor is connected via engaging gears with a part, the so-called brake hub, which is connected with the rotating parts of the brake. The engaging gears can also be designed via a fitting key.

In one other development of the invention, the brake designed as a negative brake is actuatable in closing direction via cylindrical pressure springs or via a plate spring.

In another development of the invention, the drive shaft of the steering motor is connected with an inner central wheel of a planetary transmission or is designed integrally therewith which is in operative connection with planetary gears. The planetary gears are in operative connection with a first hollow gear and a second hollow gear, one of the hollow gears being non-rotatably connected with the vehicle chassis and the other hollow gear with the output wheel. Both hollow gears having different number of teeth, the planetary transmission is designed as a Wolfrom drive whereby, upon rotation of the inner central wheel, the drive wheel rotates around its steering axis thus performing a steering motion.

BRIEF DESCRIPTION OF THE DRAWINGS

The invention will now be described, by way of example, with reference to the accompanying drawings in which.

DETAILED DESCRIPTION OF THE INVENTION

Figure 1:
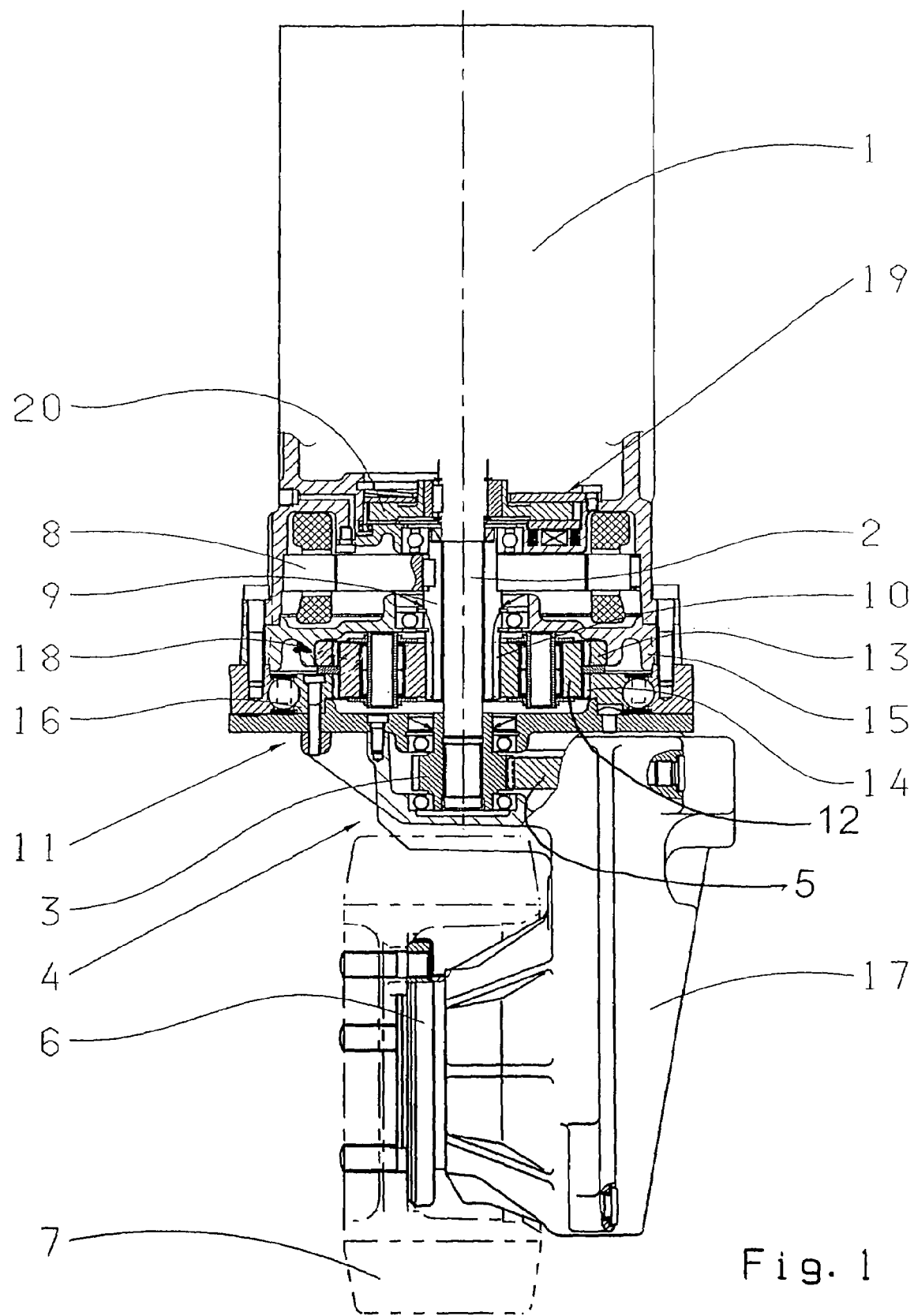
FIG. 1 is a view of the whole wheel drive.

FIG. 1:

One prime mover 1 preferably designed as electric motor drives via an (first) drive shaft 2, a first spur gear 3 of a reduction gear 4. The first spur gear 3 drives a second spur gear 5 which, via a bevel gear (not shown) drives an output 6 of the wheel drive which is connected with a drive wheel 7. A second prime mover 8 drives, via a (second) drive shaft 9, an inner central gear 10 of a 4 planetary gear 11, which is designed as a Wolfram transmission. Planets 12 mesh with a first hollow gear 13 and a second hollow gear 14, the first hollow gear 13 being non-rotatably supported in a cover 15 non-rotatably connected with a part of the vehicle chassis. The second hollow gear 14 is non-rotatably connected with a cover 16 non-rotatably connected with a housing 17 whereby the rotation of the second hollow gear 14 turns the housing 17 in direction of a steering motion. A steering gear 18 is located between the reduction gear 4 and the second prime mover 8. A brake 19 is situated between the first prime mover 1 and second prime mover 8. The first prime mover 1, the second prime mover 8, the brake 19 and the steering gear 18 are co-axially disposed. The drive shaft 2 is connected with rotating parts 20 of the brake 19.

FIG. 2:

The drive shaft 2 of the first prime mover 1 is non-rotatably connected with a hub 21, which is non-rotatably connected with the rotating parts 20 of the brake 19. A pressure plate 22 is pressed by the tension of springs 23 on the rotating parts 20 whereby the brake is actuated in an engaging direction. By electric actuation of electric magnets 24, the pressure plate 22 is detached from the rotating parts 20 whereby the brake is actuated in a disengaging direction.

FIG. 3:

The drive shaft 2 of the first prime mover 1 is connected via a fitting spring 25 with the hub 21. The hub 21 is connected with the rotating part 20 of the brake 19. Due to the tension of a plate spring 26, the pressure plate 22 is pressed on the rotating part 20 whereby the brake is actuated in an engaging direction. By pressurization of a piston 27, via an inlet 28, the pressure plate 22 is detached, via a tappet 29, from the rotating part 20 whereby the brake is actuated in the disengaging direction.

Figure 3:
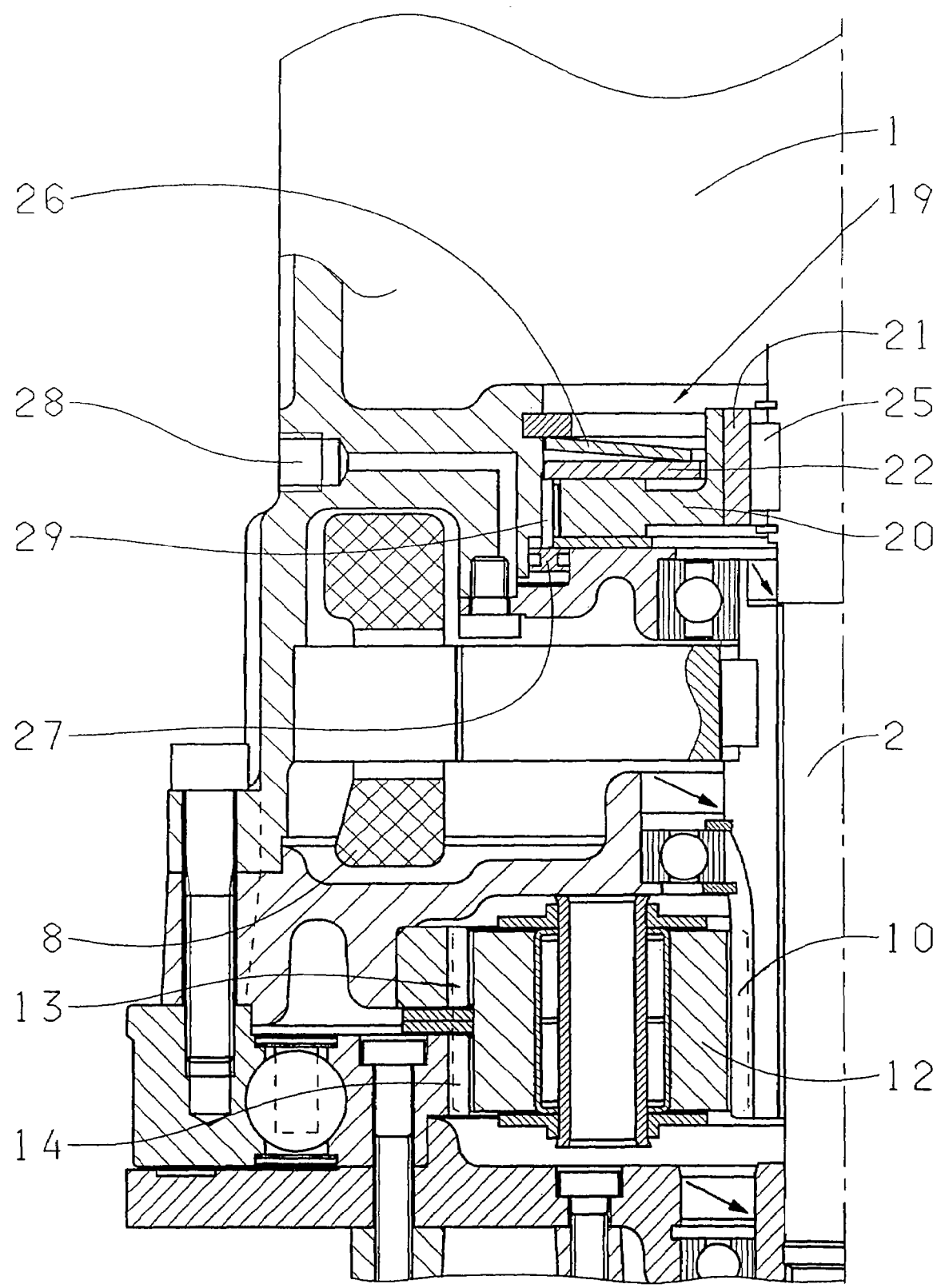
FIG. 3 is a partial cutout in the half section of the wheel drive where the brake, the steering motor and the steering gear are shown.
Figure 4:
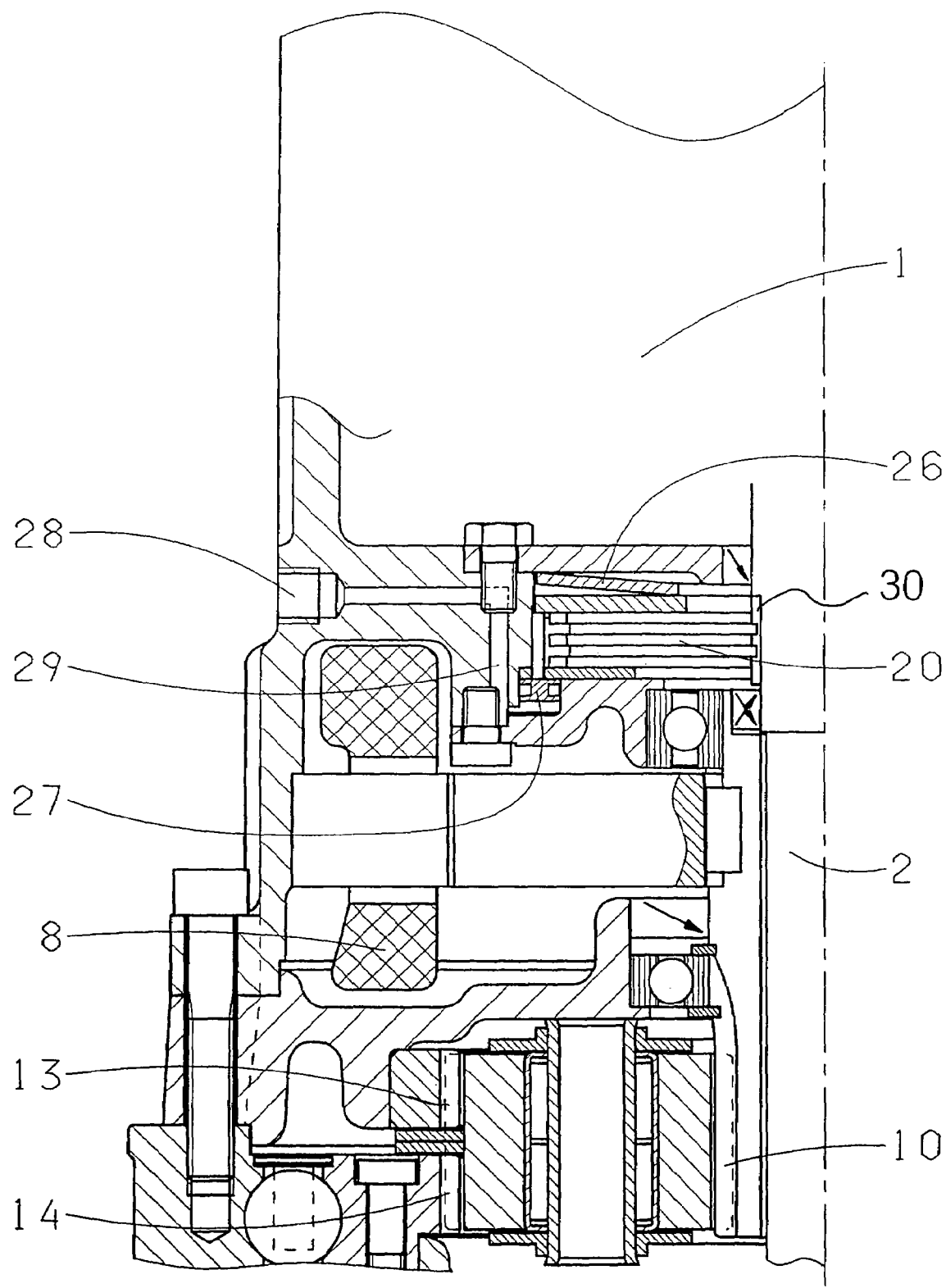
FIG. 4 is a cutout in the half section of the wheel drive where the brake, the steering motor and the steering gear are shown.

FIG. 4:

The drive shaft 2 of the first prime mover 1 has engaging gears 30 by way of which rotating parts 20, the so-called brake discs, are non-rotatably connected. The brake, like the brake in FIG. 3, is actuated via the plate spring 26 in the engaging direction and by hydraulic pressurization via the inlet 28 in the disengaging direction.

Figure 2:
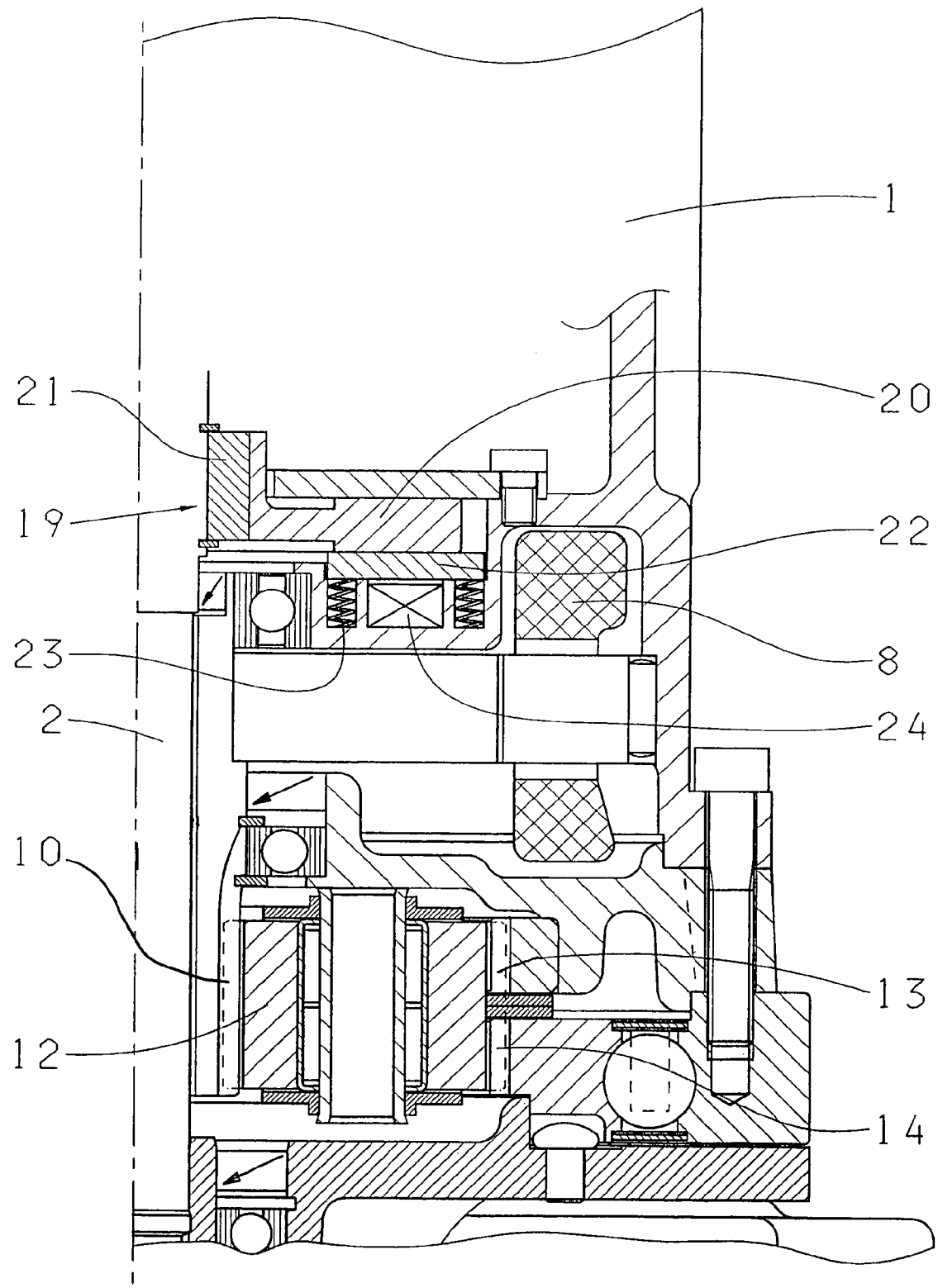
FIG. 2 is a detailed cutout of a half section of the wheel drive where the brake, the steering motor and the steering gear are shown.
Figure 5:
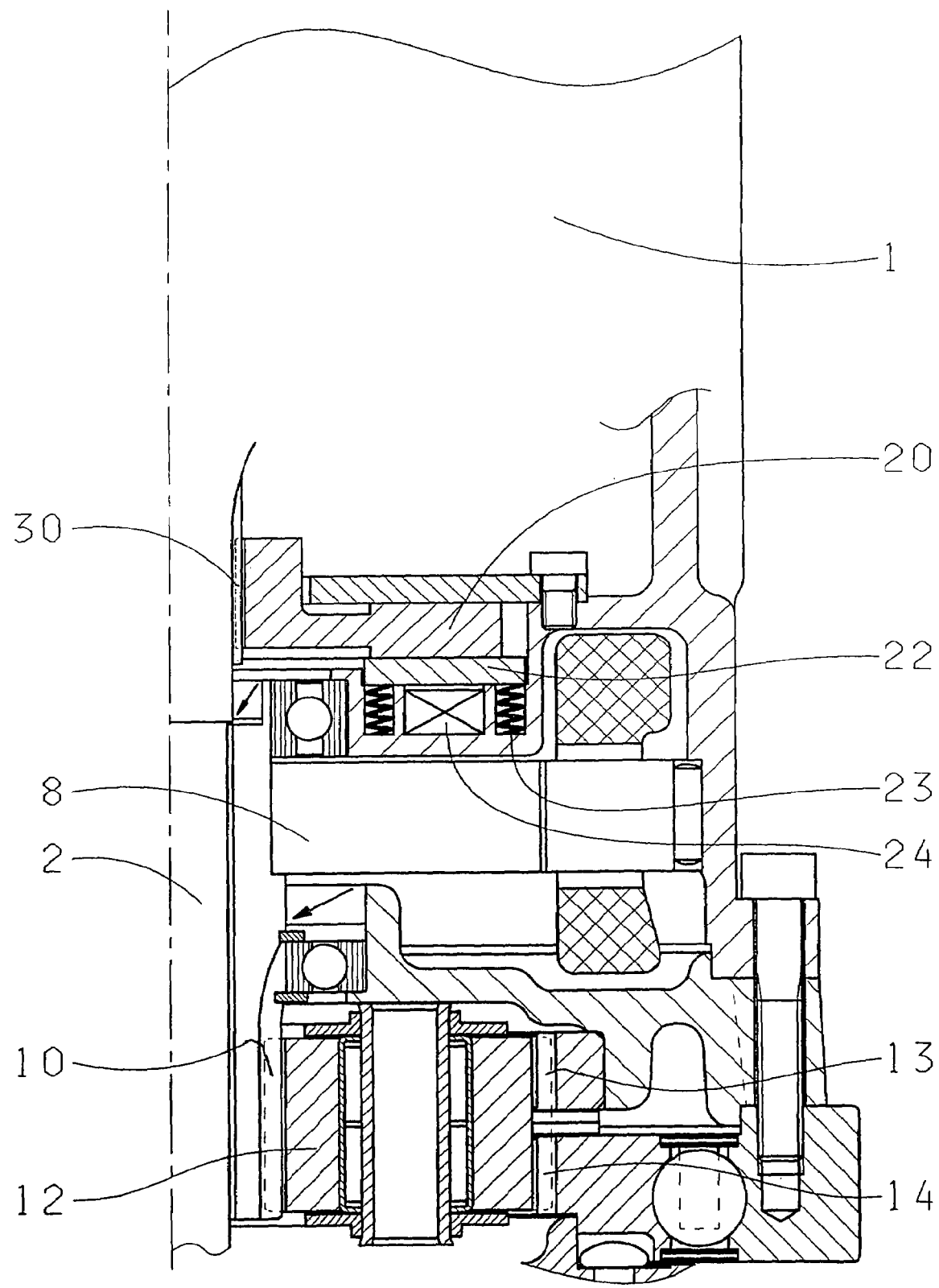
FIG. 5 is a cutout in the half section of the prime mover where the brake, the steering motor and the steering gear are shown.

FIG. 5:

The brake, according to FIG. 5, corresponds to the brake, according to FIG. 2, the rotating part 20 being non-rotatably connected via engaging gears 30 with the drive shaft 2.

REFERENCE NUMERALS 1 first prime mover
2 drive shaft
3 first spur gear
4 reduction gear
5 second spur gear
6 output
7 drive wheel
8 second prime mover
9 drive shaft
10 inner central gear
11 planetary gear
12 planets
13 first hollow gear
14 second hollow gear
15 cover
16 cover
17 housing
18 steering gear
19 brake
20 rotating parts
21 hub
22 pressure plate
23 springs
24 electric magnet
25 fitting spring
26 plate spring
27 piston
28 inlet
29 tappet
30 engaging gears

The invention claimed is:

1. A wheel drive for an industrial vehicle, the wheel drive comprising:
   a first electric prime mover (1) having a first drive shaft (2) driving an output (6), via at least one spur gear transmission (4), in a desired rotational direction which is drivingly coupled to a drive wheel (7);
   a second electric prime mover (8) driving a second drive shaft (9) being coupled with the output (6) such that by rotation of the second drive shaft (9) of the second electric prime mover (8), the output (6) rotates in a desired direction to provide a desired steering motion for the wheel drive;
   a brake (19) for braking the drive wheel (7);
   the first electric prime mover (1), the second electric prime mover (8) and the brake (19) all being disposed co-axially with the second drive shaft (9) of the second prime mover (8) and contained within a common housing with the second electric prime mover (8) being located vertically below the first electric prime mover (1); and
   the brake (19) being located between the first prime mover (1) and the second prime mover (8);
   wherein the second drive shaft (9) drives an inner central wheel (10) of a planetary transmission (11) having planetary gears (12) operative connected with a first hollow gear (13) and a second hollow gear (14), the first hollow gear (13) and the second hollow gear (14) have different numbers of teeth, and the first hollow gear (13) communicates with one part of the industrial vehicle and the second hollow gear (14) communicates with a rotating part (16).

2. A wheel drive for an industrial vehicle, the wheel drive comprising:
   a first electric prime mover (1) driving an output (6) via at least one spur gear transmission (4) in a direction of a traveling mechanism connected with a drive wheel (7);
   a second electric prime mover (8) driving a drive shaft (9) being coupled with the output (6) such that by rotation of the drive shaft (9), the output (6) rotates in a direction of a steering motion; and
   a brake (19) for braking the drive wheel (7);
   the first electric prime mover (1), the second electric prime mover (8) and the brake (19) all being disposed co-axially with the drive shaft (9) of the second prime mover (8);
   the brake (19) being located between the first prime mover (1) and the second prime mover (8);
   wherein the drive shaft (9) drives an inner central wheel (10) of a planetary transmission (11) having planetary pears (12) operative connected with a first hollow gear (13) and a second hollow gear (14), the first hollow gear (13) and the second hollow gear (14) have different numbers of teeth, and the first hollow gear (13) communicates with one part of the industrial vehicle and the second hollow gear (14) communicates with a rotating part (16); and
   the planetary transmission (11) being co-axially with the first prime mover (1).

3. A wheel drive for an industrial vehicle, the wheel drive comprising:
   a first electric prime mover (1) driving an output (6) via at least one spur gear transmission (4) in a direction of a traveling mechanism connected with a drive wheel (7);
   a second electric prime mover (8) driving a drive shaft (9) being coupled with the output (6) such that by rotation of the drive shaft (9), the output (6) rotates in a direction of a steering motion; and
   a brake (19) for braking the drive wheel (7);
   the first electric prime mover (1), the second electric prime mover (8) and the brake (19) all being disposed co-axially with the drive shaft (9) of the second prime mover (8);
   the brake (19) being located between the first prime mover (1) and the second prime mover (8);
   wherein the drive shaft (9) drives an inner central wheel (10) of a planetary transmission (11) having planetary gears (12) operative connected with a first hollow gear (13) and a second hollow gear (14), the first hollow gear (13) and the second hollow gear (14) have different numbers of teeth, and the first hollow gear (13) communicates with one part of the industrial vehicle and the second hollow pear (14) communicates with a rotating part (16); and the rotating part (16) communicating with a housing (17) of the output (6).

4. The wheel drive according to claim 1, wherein the brake (19) engages via spring force and disengages via one of electromagnetic power and hydraulic power.

5. The wheel drive according to claim 4, wherein the spring force is generated by at least one plate spring (26) or at least one spiral pressure spring (23).

6. The wheel drive according to claim 1, wherein the brake (19) is a liquid-cooled brake.

7. The wheel drive according to claim 1, wherein the brake (19) is a dry-operating disc brake, and a seal is located between the brake (19) and the at least one spur gear transmission (4).

8. The wheel drive according to claim 1, wherein the first drive shaft (2) of the first prime mover (1) is connected with the brake (19) via one of an engaging gear and a fitting spring.

9. The wheel drive according to claim 1, wherein the first drive shaft (2) of the first electric prime mover (1) extends longitudinally through an interior of the second drive shaft (9) of the second electric prime mover (8).

* * * * *